United States Patent [19]

Okuda et al.

[11] 4,140,631
[45] Feb. 20, 1979

[54] SEALANT FOR SEPARATION OF SERUM OR PLASMA, AND ITS USE

[75] Inventors: Hidefumi Okuda; Toshio Abo, both of Osaka; Rikio Shinohara, Gifu, all of Japan

[73] Assignees: Nippon Paint Co., Ltd., Osaka; Nippon Chemiphar Co., Ltd., Tokyo, both of Japan

[21] Appl. No.: 837,910

[22] Filed: Sep. 29, 1977

[30] Foreign Application Priority Data

Sep. 29, 1976 [JP] Japan ................................ 51-117614

[51] Int. Cl.$^2$ ............................................. B01D 21/26
[52] U.S. Cl. ............................ 210/83; 210/DIG. 23; 210/DIG. 24; 233/1 A; 233/1 R; 233/26
[58] Field of Search ................... 23/230 B, 258.5, 259, 23/292; 128/2 F, 214 R, DIG. 5; 210/83, 84, 514–518, DIG. 23, DIG. 24; 233/1 A, 1 R, 26; 260/42.37

[56] References Cited

U.S. PATENT DOCUMENTS 3,647,070  3/1972  Adler ...................................... 210/83
3,920,549  11/1975  Giglello ........................ 210/DIG. 23

*Primary Examiner*—Frank Sever
*Attorney, Agent, or Firm*—Wenderoth, Lind & Ponack

[57] ABSTRACT

A sealant for separation of a sample of blood into serum or plasma and clot portions, which has a specific gravity of about 1.03 to 1.08 and a viscosity of about 5,000 to 1,000,000 cps at a shearing speed of 1 second$^{-1}$ when measured at 25° C. and comprises as the essential component a polymer essentially consisting of the units of at least one of alkyl acrylates and alkyl methacrylates, and which forms a separator between the serum or plasma portion as the upper layer and the clot portion as the lower layer formed as the result of centrifugation of the blood sample so that the serum or plasma portion is readily separated from the clot portion by decantation.

12 Claims, 1 Drawing Figure

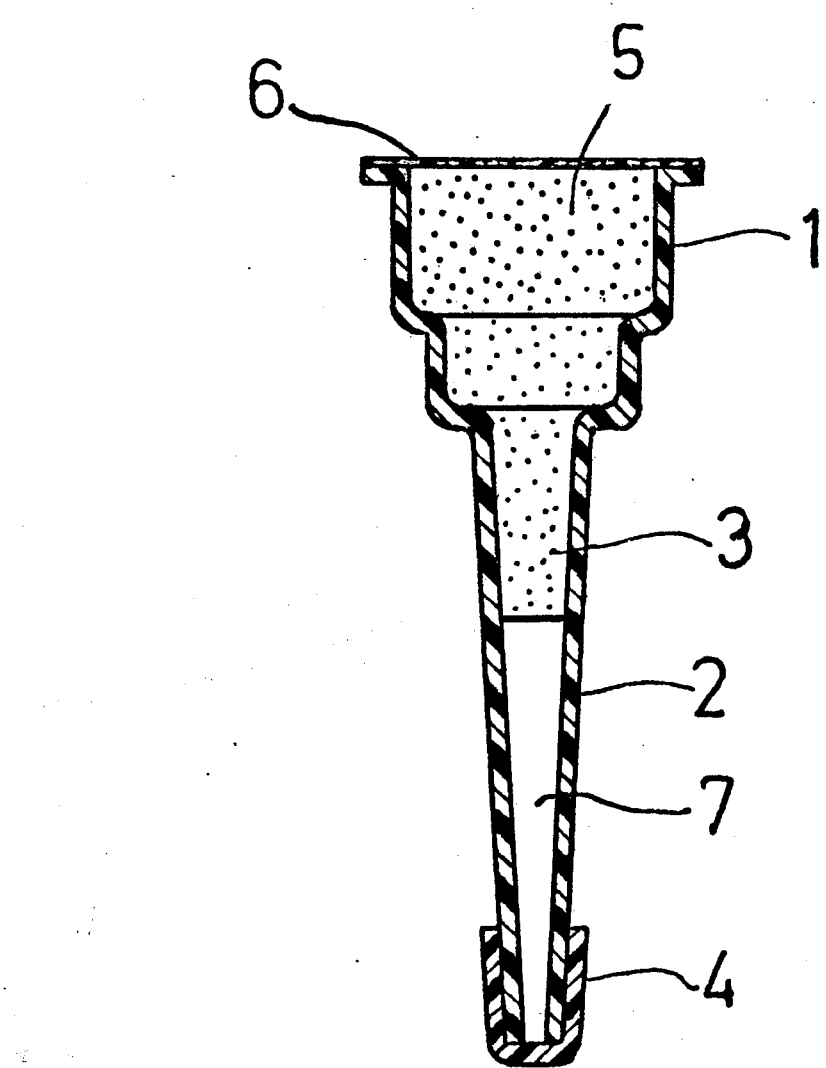

SEALANT FOR SEPARATION OF SERUM OR PLASMA, AND ITS USE

The present invention relates to a sealant for separation of serum or plasma, and its use. More particularly, it relates to a sealant comprising a polymer of alkyl acrylate and/or methacrylate as an essential component, and a method for separation of a sample of blood into serum or plasma and clot portions using the same.

The chemical analysis of the blood components is essential for medical diagnosis and treatment in these modern days. Comparison of chemical informations afforded by the blood sample of a patient with those obtained from the blood sample in a healthy state greatly contributes to judgement of the conditions of the disease.

In the clinical chemical analysis, the whole blood is unsuitable as a specimen to be tested, and serum or plasma is usually employed as the analytical sample. The serum or plasma sample for such purpose is obtainable by charging the blood taken from a patient into a test tube, centrifuging the test tube to separate serum or plasma from blood corpuscles and taking out the serum or plasma by the aid of a pipette. In this conventional separation procedure, skilled labor is required so as to collect the serum or plasma in as large amount as possible while preventing contamination with blood corpuscles. It is also required at the same time to take sufficient care for preventing pollution by way of the pipette. Usually, one clean capillary pipette is used for one sample, but the washing of pipettes takes an unexpectedly long time.

Under these circumstances, various attempts have been made for separating serum or plasma efficiently and precisely from the whole blood in a short time. A typical example of such attempts is the centrifugal separation of serum or plasma from blood corpuscles in the presence of a sealant having a specific gravity larger than that of the serum or plasma which will form the upper layer and smaller than that of the blood corpuscles which will form the lower layer. As the result of the centrifugation, the sealant forms a separator between the upper serum or plasma layer and the lower blood corpuscle layer so that the upper serum or plasma layer can be readily collected by decantation without using any pipette.

As the sealant in such method, there is used a solid one (e.g. powders, pellets, beads) or a liquid one. Examples of the solid sealant are styrene resin powders (Japanese Patent Publication No. 38841/1973), pellets or plates of a hydrogel of a crosslinked polymer of 2-hydroxyethyl methacrylate or acrylamide (U.S. Pat. No. 3,647,070), beads of polystyrene bearing an antithrombus agent or a wetting agent on the surfaces (U.S. Pat. No. 3,464,890), etc. These solid sealants are advantageous low in cost. But, their separation function is not sufficient, and the loss of serum or plasma is unavoidable to a certain extent. Further, the blood corpuscles exude through the gaps between the solid sealant and the wall of a container wherein the centrifugal separation has been effected, whereby a serious influence is afforded on the test results. Furthermore, since the separator formed by the solid sealant is readily broken by an impact or unnatural movement, great care must be taken in carrying the container.

The above drawbacks as seen in the solid sealant are usually not recognized in a liquid sealant. However, only a silicone fluid has heretofore been known as a liquid sealant usable for the above purpose. Further, even a silicone fluid does not possess appropriate specific gravity and viscosity. For instance, it may form a separator between the serum or plasma layer and the blood corpuscle layer but the viscosity is somewhat small so that the collection of the serum or plasma layer alone by decantation is difficult. For imparting appropriate specific gravity and viscosity to a silicone fluid, the incorporation of a thixotropic agent such as silica has been proposed (U.S. Pat. Nos. 3,852,194 and 3,780,935). However, the resultant mixture in a gel form is turbid so that the perfection of separation is not readily obtained. In addition, a silicone fluid is relatively expensive.

As the result of extensive study, it has now been found that a polymer of alkyl acrylate and/or methacrylate having certain specific gravity and viscosity is quite suitable as a sealant for separation of a sample of blood into serum or plasma and clot portions, since it can form a definite separator between the said portions on centrifugation, which separator is so viscous as to adhere onto the wall of a container wherein the centrifugal separation has been made and can retain satisfactorily the clot portion on the decantation for collection of the serum or plasma portion. Advantageously, the said polymer is not reactive to proteins, enzymes, lipids, inorganic ions, etc. in the blood and therefore does not afford any unfavorable influence on the test results. The present invention is based on the above finding.

According to the present invention, there is provided a sealant for separation of a sample of blood into serum or plasma and clot portions, which has a specific gravity of about 1.03 to 1.08 and a viscosity of about 5,000 to 1,000,000 cps at a shearing speed of 1 second$^{-1}$ when measured at 25° C., and comprises as the essential component a polymer essentially consisting of the units of at least one monomer of the formula:

$$CH_2=\underset{\underset{\displaystyle R_1}{|}}{C}-COOR_2 \qquad (I)$$

wherein $R_1$ is hydrogen or methyl and $R_2$ is alkyl having not more than 18 carbon atoms.

Examples of the monomer (I) are alkyl acrylates and alkyl methacrylates wherein the alkyl moiety may be, for instance, methyl, ethyl, n-propyl, isopropyl, n-butyl, isobutyl, sec-butyl, t-butyl, n-amyl, isoamyl, hexyl, 2-ethylhexyl, heptyl, octyl, capryl, nonyl, decyl, undecyl, lauryl, tridecyl, myristyl, pentadecyl, cetyl, heptadecyl or stearyl.

As stated above, the sealant of the invention is characteristic in having a specific gravity of about 1.03 to 1.08 and a viscosity of about 5,000 to 1,000,000 cps at a shearing speed of 1 second$^{-1}$ when measured at 25° C. and comprising as the essential component a polymer essentially consisting of the units of the monomer(s) (I).

When the specific gravity is lower than the said lower limit, the sealant floats in the serum or plasma portion. When higher than the said upper limit, the sealant is precipitated in the clot portion. Thus, the said specific gravity range is essential for formation of a definite separator between the serum or plasma and clot portions. A preferred range of the specific gravity is from about 1.035 to 1.06.

When the viscosity is lower than the said lower limit, the separator formed by the sealant is readily broken on decantation so that the separation of the serum or plasma portion without contamination by the clot portion becomes difficult. When higher than the said upper limit, the sealant is too viscous and cannot be easily handled. A favorable range of the viscosity is from about 20,000 to 500,000, particularly from about 60,000 to 250,000 cps.

The specific gravity and the viscosity of the sealant is dependent upon the polymer used as the essential component, of which the specific gravity and the viscosity are greatly varied with the kind of the monomer(s) (I) used for its manufacture. When, for instance, an alkyl acrylate or methacrylate of which the alkyl moiety has one or two carbon atoms is used alone, the specific gravity of the produced polymer is relatively large. When an alkyl acrylate or methacrylate of which the alkyl moiety has not less than 6 carbon atoms is used alone, the specific gravity becomes relatively small. By the combined use of monomers of which the alkyl moiety has one or two carbon atoms and of which the alkyl moiety has not less than 6 carbon atoms in an appropriate proportion, there may be obtained a polymer having a favorable specific gravity by itself. As to the viscosity, the use of an alkyl acrylate as the major monomeric component is usually preferred to that of the corresponding alkyl methacrylate in giving easily a polymer satisfying the said requirement.

The polymer as the essential component in the sealant of the invention may be produced by subjecting one or more of the monomer (I) to solution polymerization in an appropriate solvent and evaporating the solvent from the reaction mixture. The solution polymerization may be carried out by a per se conventional procedure. For instance, the monomer(s) (I) are dropwise added to a suitable solvent (e.g. toluene, xylene, butanol, ethyl acetate, butyl acetate, cellosolve acetate) in the presence of a polymerization initiator (e.g. benzoyl peroxide, azobisisobutyronitrile, cumene hydroperoxide) at an appropriate temperature (e.g. 70° to 120° C.). After completion of the addition, the reaction mixture may be, if necessary, kept at the same temperature for aging until a desired viscosity is attained. A lower temperature for polymerization than about 70° C. requires a longer reaction time (i.e. time for addition plus time for aging)), and the viscosity of the produced polymer tends to be larger. At a temperature higher than about 120° C., the control of the temperature is difficult and the viscosity of the polymer is apt to be smaller. When the polymerization temperature is kept between about 70° and 120° C., the time for polymerization may be usually from about 3 to 5 hours. The amount of the polymerization initiator may be from about 0.5 to 2% by weight to the weight of the monomer(s) (I). When it is used in a too excessive amount, the control of the temperature becomes difficult and the viscosity of the polymer tends to become small. The amount of the solvent may be in a range of about 30 to 50% by weight to the total amount of the solvent and the monomers. Since the solvent is eliminated by evaporation under reduced pressure after completion of the polymerization, its amount is desirable to be as small as possible. But, with an amount smaller than about 30% by weight, the control of the temperature is difficult and the viscosity of the polymer tends to be too large.

After the polymerization is completed, the solvent is evaporated from the reaction mixture to give the objective polymer. When, for instance, the concentration of the monomer(s) (I) is about 60% by weight based on the total amount of the monomer(s) (I) and the solvent, there is usually obtained the reaction mixture having a solid content of about 55 to 59% by weight. Evaporation of the solvent from such reaction mixture can give a polymer having a nonvolatile content of not less than about 98.0% by weight, preferably not less than about 99.5% by weight.

The thus obtained polymer usually has a viscosity of not less than about 3,000 cps at 25° C. A polymer having a lesser viscosity is obtainable by the use of a chain transfer agent such as a mercaptan in the said solution polymerization. However, such chain transfer agent affords an unfavorable influence on the test results when the polymer is employed as the sealant.

When the produced polymer itself has appropriate specific gravity and viscosity as stated above, it can be utilized alone as the sealant of the invention. If, however, at least one of specific gravity and/or viscosity of the produced polymer is not appropriate, such polymer may be blended with another polymer essentially consisting of the units of alkyl acrylate and/or methacrylate, which is obtainable by the substantially same solution polymerization procedure as explained above but has more or less different specific gravity and viscosity. In other words, the polymer as the essential component in the sealant of the invention may be a mixture of two or more kinds of polymers of alkyl acrylate and/or alkyl methacrylate having different specific gravity and viscosity insofar as the resultant mixture has appropriate values.

Also, a filler may be incorporated into the polymer to result in the desired specific gravity and viscosity, particularly when the specific gravity and/or viscosity of the polymer are lower than the desired values. As the filler, the use of silica in fine particles, particularly having a high purity of about 99% by weight or more, as disclosed in U.S. Pat. No. 3,780,935 is favorable due to its inert property to the blood components. The amount of silica is preferred to be not more than about 30% by weight based on the weight of the polymer, since otherwise the viscosity becomes too large so that the handling is difficult. Although the incorporation of silica is effective to increase the specific gravity and the viscosity as stated above, such incorporation into the polymer having a viscosity of not less than about 20,000 cps should be avoided, because the viscosity becomes too high. Thus, the incorporation of silica is recommendable only when the polymer has a viscosity of not less than about 3,000 cps and less than about 20,000 cps. Such polymer usually has a specific gravity of about 1.000 to 1.030.

Different from a mixture of silicone and silica as disclosed in U.S. Pat. No. 3,780,935, a mixture of the polymer and silica as herein obtained is transparent, and therefore the perfection of the separation can be readily recognized and determined.

As understood from the above, the polymer having the values not within the said desired ranges concerning specific gravity and viscosity is still usable in the present invention by control of those values.

When the viscosity of the sealant is relatively low, polystyrene beads or pellets may be added thereto, whereby the strength or retention effect of the separator formed by the sealant may be enhanced. The amount of the beads or pellets to be added may be usually from about 80 to 120% by weight to the amount of the polymer.

For separation of a sample of blood by the use of the sealant of the invention, the blood sample charged in an appropriate container adapted to be centrifuged (e.g. a test tube) is subjected to centrifugation in the presence of the sealant, whereby a serum or plasma portion as the upper layer and a clot portion as the lower layer are separated by the intervention of a separator formed by the sealant between the said portions. The amount of the sealant to be used for the separation may be usually in a range of about 0.5 to 1.5 g per 10 ml of the sample blood. Since the separator is so viscous as to adhere on the wall of the container, the clot portion can be retained in the container while the serum or plasma portion can be readily removed from the container by decantation.

Practically, the separation may be effected by various procedures, of which a typical example comprises introducing a sample of blood into a container adapted to be centrifuged and containing the sealant, subjecting the container to centrifugation whereby the blood sample is separated into the serum or plasma portion as the upper layer and the clot portion as the lower layer by intervention of a separator formed by the sealant between the said two layers, and then removing the serum or plasma portion into any other container, particularly suitable for subjecting to chemical analysis, by decantation.

Another typical procedure comprises introducing the sealant into a container adapted to be centrifuged and containing a sample of blood, subjecting the container to centrifugation whereby the blood sample is separated into the serum or plasma portion as the upper layer and the clot portion as the lower layer by intervention of a separator formed by the sealant between the said two layers, and then removing the serum or plasma portion into any other container, particularly suitable for subjecting to chemical analysis, by decantation.

As understood from these procedures, the sealant may be supplied, in a packaged form, in a container adapted to be centrifuged or in a container which is adaptable to the opening of a container adapted to be centrifuged and containing a sample of blood.

In general, however, it is favored to put the sealant in a container adapted to be centrifuged, particularly at the bottom, prior to the introduction of a sample of blood therein. If the sealant is introduced into a container adapted to be centrifuged wherein a sample of blood is already charged, a part of the sealant may sometimes fail to overcome the surface tension of the blood sample even when the centrifugal operation is applied thereto, so that it will float on the surface of the serum or plasma portion as the upper layer and, on decantation, be removed from the container together with the serum or plasma portion.

Still, the separation method of this invention is applicable not only to the collection of a serum portion but also the collection of a plasma portion. For collection of the plasma portion, a conventional anticoagulant against the coagulation of blood may be added to a sample of blood at any stage prior to the centrifugation. When the collection of a serum portion is aimed at, such addition is not required.

In comparison with the conventional separation method using a pipette, the separation method of this invention contributes greatly to saving time and labor. Further, the cost is substantially reduced, since the polymer used in the sealant of the invention is quite cheap. In addition, the sealant of the invention can be supplied in a packaged form in a disposable container adapted to be centrifuged, and therefore its use can avoid the infection with an HB antibody.

Practical and presently preferred embodiments of this invention are illustratively shown in the following Examples wherein part(s) and percents(s) are by weight.

The specific gravity was determined at 25° C. by the so-called cupric sulfate method: i.e. cupric sulfate solutions of various concentrations are prepared, a drop of the specimen is added thereto, and the specific gravity of the cupric sulfate solution in which the drop has neither floated nor sunk is taken as the specific gravity of the specimen.

The viscosity was measured at 25° C. by the use of a viscometer "Shimadzu reometer RM-1" manufactured by Shimadzu Seisakusho Ltd (i.e. a rotatory viscometer usable for measurement of the viscosity not only of a Newtonian liquid but also of a non-Newtonian liquid). In case of the specimen consisting of the polymer, the viscosity is not varied with the shearing speed since the polymer is a Newtonian liquid. In case of the specimen consisting of a mixture of the polymer and silica, the viscosity is varied with the shearing speed since the mixture is a non-Newtonian liquid. Therefore, measurement was made at a shearing speed of 1 second$^{-1}$.

Part I (Preparation of sealants)

Example I-1

In a four-necked flask equipped with a stirrer, a reflux condenser, a thermometer and a dropping funnel, toluene (40 parts) is charged, and the temperature is elevated up to 112° C. under stirring. A mixture of n-butyl acrylate (60 parts) and t-butylperoxy 2-ethylhexanoate (tradename "Perbutyl O" manufactured by Nippon Oils and Fats Co., Ltd.) (0.6 part) is dropwise added thereto continuously in 3 hours. After completion of the addition, the resultant mixture is kept for 2 hours at the same temperature under stirring for aging to obtain a polymer solution (nonvolatile content, 59%). The thus obtained solution is evaporated for 5 hours under reduced pressure for elimination of the solvent while elevating the temperature gradually up to 140° C. to give a polymer (non-volatile content, 99.7%) having a specific gravity of 1.040 to 1.045 and a viscosity of 105,000 cps.

This polymer can constitute the sealant of the invention by itself.

EXAMPLE I-2

In the same flask as in Example I-1, toluene (40 parts) is charged, and the temperature is elevated up to 112° C. under stirring. A mixture of n-butyl acrylate (42 parts), ethyl acrylate (18 parts) and benzoyl peroxide (0.6 part) is dropwise added thereto continuously in 3 hours. After completion of the addition, the resultant mixture is kept for 2 hours at the same temperature under stirring for aging to obtain a polymer solution (non-volatile content, 59%). The thus obtained solution is evaporated for elimination of the solvent in the same manner as in Example I-1 to give a polymer (non-volatile content, 99.6%) having a specific gravity of 1.055 to 1.060 and a viscosity of 230,000 cps.

This polymer can constitute the sealant of the invention by itself.

EXAMPLE I-3

The solution polymerization and the subsequent elimination of the solvent are carried out in Example I-2 but using a mixture of 2-ethylhexyl acrylate (36 parts), methyl acrylate (24 parts) and "Perbutyl O" used in Example I-1 (1.2 parts) to give a polymer (non-volatile content, 99.7%) having a specific gravity of 1.050 to 1.055 and a viscosity of 320,000 cps.

This polymer can constitute the sealant of the invention by itself.

EXAMPLE I-4

The solution polymerization and the subsequent elimination of the solvent are carried out as in Example I-2 but using a mixture of n-butyl acrylate (42 parts), n-butyl methacrylate (18 parts) and "Perbutyl O" used in Example I-1 (1.2 parts) to give a polymer (non-volatile content, 99.6%) having a specific gravity of 1.030 to 1.035 and a viscosity of 146,000 cps.

This polymer can constitute the sealant of the invention by itself.

EXAMPLE I-5

The solution polymerization and the subsequent elimination of the solvent are carried out as in Example I-2 but using a mixture of n-butyl acrylate (48 parts), ethyl methacrylate (12 parts) and benzoyl peroxide (1.2 parts) to give a polymer (non-volatile content, 99.8%) having a specific gravity of 1.050 to 1.055 and a viscosity of 168,000 cps.

This polymer can constitute the sealant of the invention by itself.

EXAMPLE I-6

The solution polymerization and the subsequent elimination of the solvent are carried out as in Example I-2 but using a mixture of 2-ethylhexyl acrylate (42 parts), methyl acrylate (18 parts) and benzoyl peroxide (1.2 parts) to give a polymer (non-volatile content, 99.7%) having a specific gravity of 1.035 to 1.040 and a viscosity of 165,000 cps.

This polymer can constitute the sealant of the invention by itself.

EXAMPLE I-7

The solution polymerization and the subsequent elimination of the solvent are carried out in Example I-2 but using a mixture of n-butyl acrylate (36 parts), methyl acrylate (12 parts), lauryl methacrylate (12 parts) and azobisisobutyronitrile (1.2 parts) to give a polymer (non-volatile content, 99.5%) having a specific gravity of 1.040 to 1.045 and a viscosity of 178,000 cps.

This polymer can constitute the sealant of the invention by itself.

EXAMPLE I-8

The solution polymerization and the subsequent elimination of the solvent are carried out as in Example I-2 but using a mixture of n-butyl acrylate (42 parts), 2-ethylhexyl acrylate (18 parts) and "Perbutyl O" used in Example I-1 (1.2 parts) to give a polymer (non-volatile content, 99.7%) having a specific gravity of 1.020 to 1.025 and a viscosity of 18,750 cps.

Into the polymer (100 parts), hydrophobic silica (tradename "Aerosil 200" manufactured by Nippon Aerosil Co., Ltd.) (10 parts) is dispersed to make a mixture having a specific gravity of 1.045 to 1.050 and a viscosity of 120,000 cps.

This mixture can constitute the sealant of the invention by itself.

EXAMPLE I-9

The solution polymerization and the subsequent elimination of the solvent are carried out as in Example I-2 but using a mixture of n-butyl acrylate (30 parts), 2-ethylhexyl acrylate (30 parts) and "Perbutyl O" used in Example I-1 (1.2 parts) to give a polymer (non-volatile content, 99.7%) having a specific gravity of 1.010 to 1.015 and a viscosity of 7,750 cps.

Into the polymer (100 parts), hydrophobic silica (tradename "Aerosil R972" manufactured by Nippon Aerosil Co., Ltd.) (20 parts) is dispersed to make a mixture having a specific gravity of 1.045 to 1.050 and a viscosity of 180,000 cps.

This mixture can constitute the sealant of the invention by itself.

Part II (Separation of blood samples into serum or plasma and clot portions):

EXAMPLE II-1

To a test tube made of glass or a plastic resin (e.g. polyethylene, polypropylene, polystyrene) containing one gram of the polymer prepared in Example I-1 at the bottom, a sample of blood (10 ml) collected by an injector is added. After being allowed to stand at room temperature for 30 to 60 minutes, the test tube is centrifuged at 2,500 to 3,000 rotations per minute for 10 minutes, whereby the serum portion as the upper layer and the clot portion as the lower layer are definitely separated by intervention of a separator formed by the polymer between them. Then, the upper serum portion is removed to a container suitable for analysis by decantation.

For obtaining a plasma portion instead of the serum portion in the above operation, the addition of a conventional anticoagulant is carried out in place of allowing the test tube to stand prior to the centrifugation.

On the decantation, the separator is adhered onto the wall of the test tube so that the clot portion can be retained in the test tube without coming into the serum or plasma portion. Further, the polymer is liquid and therefore does not cause any break of the blood corpuscles on collision during the centrifugation. Furthermore, the separation of the serum or plasma portion from the clot portion can be accomplished perfectly and rapidly without any damage to the serum or plasma and clot portions.

EXAMPLE II-2

The accompanying drawing is an enlarged sectional view of a container containing the sealant therein. A container (1) in a funnel shape has a nozzle (2) and accommodates a sealant (3) such as the polymer obtained in Example I-2. At the terminal end of the nozzle (2), there is provided a cap (4), which prevents the sealant (3) from falling through the nozzle (2). The container (1) has an open end (5) over which is placed and adhered a seal (6). At the nozzle portion, there is present air (7), which has been unavoidably enclosed on introduction of the sealant into the container (1) from the open end (5).

Taking off the cap (4), the nozzle (2) is inserted into the opening end of a test tube accommodating a sample of blood to adapt the container (1) onto the test tube. The tip of the nozzle (2) is dipped in the blood sample so that the influence by the surface tension of the blood sample is avoided and no floating of the sealant on the surface of the blood sample occurs. Then, the seal (6) is pinholed at the center, and centrifugation is carried out, whereby the sealant (3) in the container (1) comes into the test tube and forms a separator at the interface between a serum or plasma portion as the upper layer and a clot portion as the lower layer. Then, the container is taken off from the test tube, and the serum or plasma portion is removed to any other container by decantation, whereby the separation between the serum or plasma and clot portions is completed.

PART III (Clinical test):

the said two layers. The upper serum layer was taken out by decantation and used as a test sample.

On the other hand, the blood sampled from the same patient was as such subjected to centrifugation in the absence of the polymer, and the separated upper serum layer was taken out by a pipette and used as a sample for comparison.

The serum samples as obtained above were subjected to various tests, and the results are shown in Table 1, from which it is understood that the polymer affords no material influence on the test data.

Table 1

| Case | | A | | B | | C | | D | |
|------|------|--------|--------|--------|--------|--------|--------|--------|--------|
| *1) Test | Unit | Polymer used | Polymer not used | Polymer used | Polymer not used | Polymer used | Polymer not used | Polymer used | Polymer not used |
| BUN | mg/dl | 21 | 21 | 19 | 19 | 9 | 9 | 14 | 14 |
| UA | mg/dl | 4.0 | 4.1 | 7.8 | 7.7 | 4.5 | 4.5 | 5.3 | 5.4 |
| Crea | mg/dl | 0.8 | 0.8 | 1.0 | 1.0 | 0.7 | 0.7 | 0.8 | 0.8 |
| TP | g/dl | 7.3 | 7.4 | 7.5 | 7.2 | 7.2 | 7.3 | 7.3 | 7.4 |
| Alb | g/dl | 4.5 | 4.6 | 4.9 | 4.8 | 5.0 | 5.1 | 4.7 | 4.7 |
| IgG | mg/dl | 1040 | 1200 | 1520 | 1520 | 880 | 880 | 1660 | 1720 |
| IgA | mg/dl | 164 | 155 | 200 | 190 | 173 | 164 | 367 | 356 |
| IgM | mg/dl | 126 | 126 | 104 | 109 | 109 | 99 | 208 | 208 |
| GOT | U | 24 | 22 | 9 | 11 | 13 | 9 | 16 | 16 |
| GPT | U | 9 | 9 | 4 | 6 | 2 | 4 | 6 | 4 |
| LDH | U | 128 | 119 | 115 | 95 | 95 | 84 | 108 | 108 |
| LAP | U | 22 | 22 | 22 | 22 | 20 | 22 | 24 | 22 |
| ALP | U | 41 | 41 | 38 | 39 | 41 | 40 | 50 | 51 |
| $\gamma$-GTP | U | 4 | 7 | 7 | 7 | 4 | 7 | 7 | 7 |
| $\beta$-Lipo | mg/dl | 350 | 300 | 620 | 500 | 200 | 200 | 400 | 350 |
| PL | mg/dl | 184 | 181 | 218 | 214 | 211 | 217 | 225 | 217 |
| T-Ch | mg/dl | 162 | 156 | 185 | 184 | 176 | 168 | 207 | 208 |
| TG | mg/dl | 126 | 119 | 83 | 85 | 129 | 123 | 97 | 95 |
| FFA | mEq/l | 0.82 | 0.63 | 0.24 | 0.31 | 0.31 | 0.28 | 0.15 | 0.13 |
| Na | mEq/l | 140 | 142 | 143 | 142 | 148 | 145 | 142 | 136 |
| K | mEq/l | 4.2 | 4.1 | 3.9 | 4.0 | 4.2 | 3.8 | 3.9 | 3.8 |
| Cl | mEq/l | 108 | 107 | 104 | 105 | 108 | 108 | 106 | 104 |
| Fe | $\mu$g/dl | 154 | 150 | 85 | 87 | 110 | 117 | 150 | 151 |

Note:
*1) BUN, blood urea nitrogen test (diacetylmonoxime method);
UA, uric acid test (reduction method);
Crea, creatinine test (Jaffe reaction);
TP, total protein (Biuret method);
Alb, alubumin test (HABCA method);
IgG, immunoglobulin G test (SRID method);
IgA, immunoglobulin A test (SRID method);
IgM, immunoglobulin M test (SRID method);
GOT, glutamate oxaloacetate transaminase test (UV method);
GPT, glutamate pyruvate transaminase test (UV method);
LDH, lactate dehydrogenase test (UV method);
LAP, leucine aminopeptidase test (Bassy-lowry method);
ALP, alkaline phosphatase test (Goldbarg method);
$\gamma$-GTP, $\gamma$-glutamyl transpeptidase test (UV method);
$\beta$-Lipo, $\beta$-lipoprotein test (immunocrite method);
PL, phospholipid test (enzyme method);
T-Ch, total cholesterol test (enzyme method);
TG, triglyceride test (Sardesai-Manning method);
FFA, free fatid acid test ($Cu^{++}$- Basokproin method);
Na, sodium test (flame spectrophotometry method);
K, potassium test (flame spectrophotometry method);
Cl, chlorine test (titration method);
Fe, iron test (Matsubara method).

Example III-1

In a test tube, there were charged the polymer obtained in Example I-1 (1.0 g) and the blood (10 ml) sampled from the patient (A, B, C or D) to be tested, and the resulting mixture was subjected to centrifugation, whereby a serum portion as the upper layer and a clot portion as the lower layer were separated by intervention of a separator formed by the polymer between

EXAMPLE III-2

As in Example III-1, the tests were carried out using the serum samples separated by using the polymer as prepared in Example I-2 and separated by not using any sealant.

The results are shown in Table 2, from which it is understood that the polymer affords no material influence on the test results.

Table 2

| Case | | E | | F | | G | | H | |
|------|------|--------|--------|--------|--------|--------|--------|--------|--------|
| *1) Test | Unit | Polymer used | Polymer not used | Polymer used | Polymer not used | Polymer used | Polymer not used | Polymer used | Polymer not used |
| TP | g/dl | 8.1 | 8.1 | 6.8 | 6.6 | 7.6 | 7.6 | 7.4 | 7.2 |
| ZTT | U | 6.7 | 6.6 | 5.0 | 5.3 | 4.2 | 4.0 | 3.5 | 3.7 |
| TTT | U | 5.1 | 5.2 | 1.1 | 1.3 | 0.9 | 0.9 | 0.7 | 0.9 |
| CCF |  | (−) | (−) | (−) | (−) | (−) | (−) | (−) | (−) |
| MG | U | 5 | 5 | 6 | 6 | 5 | 6 | 4 | 4 |
| T-Ch | mg/dl | 212 | 216 | 156 | 155 | 162 | 171 | 123 | 120 |

Table 2-continued

| *1) Test | Unit | Case E Polymer used | Polymer not used | F Polymer used | Polymer not used | G Polymer used | Polymer not used | H Polymer used | Polymer not used |
|---|---|---|---|---|---|---|---|---|---|
| GOT | U | 18 | 17 | 25 | 25 | 23 | 21 | 32 | 29 |
| GPT | U | 14 | 16 | 16 | 14 | 9 | 10 | 12 | 12 |
| LAP | U | 176 | 178 | 199 | 194 | 103 | 109 | 171 | 164 |
| LDH | U | 294 | 288 | 303 | 313 | 431 | 411 | 413 | 359 |
| CPK | U | 74 | 77 | 28 | 25 | 29 | 33 | 24 | 21 |
| ALP | U | 14 | 14 | 7 | 6 | 7 | 6 | 9 | 9 |
| ACP | U | 3.8 | 3.5 | 2.4 | 2.4 | — | — | 3.2 | 2.8 |
| γ-GTP | mU/ml | 47 | 46 | 11 | 13 | 19 | 21 | 85 | 83 |
| BB | mg/dl | 1.1 | 0.9 | 0.3 | 0.5 | 0.5 | 0.4 | 0.9 | 1.1 |
| Na | mEq/l | 141 | 140 | 142 | 140 | 138 | 139 | — | — |
| K | mEq/l | 3.9 | 3.9 | 4.3 | 4.4 | 4.0 | 4.0 | — | — |
| Ca | mEq/l | 4.6 | 4.8 | 4.7 | 4.7 | 4.9 | 4.7 | — | — |
| Cl | mEq/l | 102 | 101 | 101 | 103 | 102 | 101 | — | — |
| BUN | mg/dl | 14.4 | 14.0 | 13.7 | 13.9 | 13.1 | 12.0 | — | — |
| Crea | mg/dl | 0.6 | 0.7 | 0.6 | 0.6 | 0.9 | 1.1 | — | — |
| UA | mg/dl | 4.4 | 4.1 | 4.3 | 4.4 | 3.7 | 3.8 | — | — |
| P | mg/dl | 3.5 | 3.7 | 2.7 | 2.9 | 3.0 | 3.0 | — | — |
| Mg | mEq/l | 2.6 | 2.6 | 2.8 | 2.6 | 2.7 | 2.5 | — | — |
| Fe | μg/dl | 106 | 118 | 136 | 129 | 125 | 126 | — | — |
| β-Lipo | mg/dl | 350 | 340 | 400 | 400 | 380 | 360 | — | — |
| TG | mg/dl | 130 | 151 | 166 | 170 | 207 | 213 | — | — |
| PL | mg/dl | 209 | 210 | 208 | 213 | 224 | 211 | — | — |
| Amyl | U | 93 | 106 | 113 | 129 | 180 | 165 | — | — |

Note:
*1) ZTT, zinc sulfate turbidity test (Kunkel method);
TTT, thymol turbidity test (Maclagan method);
CCF, cephalin cholesterol flocculation test (Hanger method);
MG, meulengracht index (acetone method);
CPK, creatine phosphokinase test (UV method);
ACP, acid phosphatase test (Bessy-lowry method);
BB, bilirubin test (spectrophotometry method);
CA, calcium test (direct method);
P, phosphorus test (Tanssky method);
Mg, magnesium test (titan yellow method);
Amyl, amylase test (chromogenic method).
Other abbreviations have the same meanings as indicated in Note below Table 1.

EXAMPLE III-3

As in Example III-1, the tests were carried out using the serum samples separated by using the mixture as prepared in Example I-8 and separated by not using any sealant.

The results are shown in Table 3, from which it is understood that the mixture affords no material influence on the test results.

What is claimed is:

1. A method for separation of a sample of blood into serum or plasma and clot portions which comprises subjecting the blood sample to centrifugation in the presence of a sealant which has a specific gravity of about 1.03 to 1.08 and a viscosity of about 5,000 to 1,000,000 cps at a shearing speed of 1 second$^{-1}$ when measured at 25° C., and consists essentially of a polymer material consisting essentially of units of at least one of Table 3

| *1) Test | Unit | Case I Mixture used | Mixture not used | J Mixture used | Mixture not used | K Mixture used | Mixture not used | L Mixture used | Mixture not used |
|---|---|---|---|---|---|---|---|---|---|
| TP | g/dl | 7.5 | 7.6 | 6.8 | 6.8 | 7.7 | 7.6 | 7.9 | 7.9 |
| ZTT | U | 6.7 | 6.6 | 4.3 | 4.1 | 4.8 | 5.0 | 4.2 | 4.3 |
| TTT | U | 5.3 | 5.1 | 4.5 | 4.6 | 1.0 | 1.0 | 0.7 | 0.8 |
| CCF | | (+) | (+) | (−) | (−) | (−) | (−) | (−) | (−) |
| MG | U | 5 | 5 | 5 | 5 | 4 | 5 | 6 | 6 |
| T-Ch | mg/dl | 210 | 213 | 176 | 172 | 131 | 130 | 150 | 152 |
| GOT | U | 20 | 21 | 18 | 18 | 16 | 16 | 25 | 24 |
| GPT | U | 12 | 12 | 10 | 10 | 15 | 16 | 12 | 11 |
| LAP | U | 168 | 170 | 183 | 180 | 110 | 115 | 150 | 146 |
| LDH | U | 285 | 284 | 276 | 273 | 370 | 376 | 403 | 400 |
| CPK | U | 69 | 71 | 35 | 33 | 29 | 30 | 28 | 27 |
| ALP | U | 16 | 15 | 10 | 10 | 7 | 6 | 8 | 8 |
| ACP | U | 3.5 | 3.4 | 2.6 | 2.6 | 2.5 | 2.7 | 3.0 | 3.1 |
| γ-GTP | mU/ml | 45 | 44 | 15 | 15 | 20 | 19 | 81 | 83 |
| BB | mg/dl | 1.2 | 1.1 | 0.5 | 0.6 | 0.5 | 0.5 | 0.8 | 1.0 |
| Na | mEq/l | 138 | 139 | 140 | 142 | 131 | 131 | 135 | 136 |
| K | mEq/l | 4.0 | 4.0 | 4.2 | 4.1 | 4.0 | 4.1 | 3.8 | 3.8 |
| Ca | mEq/l | 4.3 | 4.1 | 4.5 | 4.5 | 4.8 | 4.8 | 4.5 | 4.4 |
| Cl | mEq/l | 100 | 101 | 102 | 102 | 102 | 101 | 103 | 103 |
| BUN | mg/dl | 14.0 | 13.9 | 14.0 | 13.9 | 13.2 | 13.2 | 13.5 | 13.0 |
| Crea | mg/dl | 0.7 | 0.7 | 0.6 | 0.6 | 0.8 | 0.9 | 1.0 | 1.1 |
| UA | mg/dl | 4.3 | 4.2 | 4.3 | 4.2 | 4.0 | 4.1 | 3.8 | 3.8 |
| P | mg/dl | 3.6 | 3.4 | 2.9 | 2.9 | 3.1 | 3.1 | 3.0 | 3.1 |
| Mg | mEq/l | 2.7 | 2.7 | 2.6 | 2.7 | 2.7 | 2.7 | 2.5 | 2.4 |
| Fe | g/dl | 110 | 112 | 128 | 126 | 125 | 123 | 130 | 132 |
| β-Lipo | mg/dl | 340 | 350 | 380 | 360 | 390 | 390 | 350 | 340 |
| TG | mg/dl | 142 | 146 | 158 | 155 | 201 | 198 | 151 | 150 |
| PL | mg/dl | 198 | 201 | 205 | 208 | 216 | 215 | 201 | 200 |
| Amyl | U | 102 | 99 | 121 | 118 | 176 | 178 | 126 | 122 |

Note:
*1) All the abbreviations have the same meanings as indicated in Note below Table 2.

unsubstituted alkyl acrylates and unsubstituted alkyl methacrylates, the alkyl moiety having not more than 18 carbon atoms, said polymer material having a specific gravity of about 1.03 to 1.08 and a viscosity of about 5,000 to 1,000,000 cps at a shearing speed of 1 second$^{-1}$ when measured at 25° C., whereby the blood sample is separated into the serum or plasma portion as the upper layer and the clot portion as the lower layer by intervention of a separator formed by the sealant between the said two layers, and collecting the serum or plasma portion by decantation.

2. The method according to claim 1, wherein the blood sample contains an anticoagulant.

3. A method for separation of a sample of blood into serum or plasma and clot portions which comprises introducing the blood sample into a container adapted to be centrifuged and containing a sealant which has a specific gravity of about 1.03 to 1.08 and a viscosity of about 5,000 to 1,000,000 cps at a shearing speed of 1 second$^{-1}$ when measured at 25° C., and consists essentially of a polymer material consisting essentially of units of at least one of unsubstituted alkyl acrylates and unsubstituted alkyl methacrylates, the alkyl moiety having not more than 18 carbon atoms, said polymer material having a specific gravity of about 1.03 to 1.08 and a viscosity of about 5,000 to 1,000,000 cps at a shearing speed of 1 second$^{-1}$ when measured at 25° C., subjecting the container to centrifugation whereby the blood sample is separated into the serum or plasma portion as the upper layer and the clot portion as the lower layer by intervention of a separator formed by the sealant between the said two layers, and then transferring the serum or plasma portion into another container by decantation.

4. The method according to claim 3, wherein the container adapted to be centrifuged is a test tube.

5. A method for separation of a sample of blood into serum or plasma and clot portions which comprises introducing a sealant into a container adapted to be centrifuged and containing the blood sample, said sealant being a sealant which has a specific gravity of about 1.03 to 1.08 and a viscosity of about 5,000 to 1,000,000 cps at a shearing speed of 1 second$^{-1}$ when measured at 25° C., and consists essentially of a polymer material consisting essentially of units of at least one of unsubstituted alkyl acrylates and unsubstituted alkyl methacrylates, the alkyl moiety having not more than 18 carbon atoms, said polymer material having a specific gravity of about 1.03 to 1.08 and a viscosity of about 5,000 to 1,000,000 cps at a shearing speed of 1 second$^{-1}$ when measured at 25° C., subjecting the container to centrifugation whereby the blood sample is separated into the serum or plasma portion as the upper layer and the clot portion as the lower layer by intervention of a separator formed by the sealant between the said two layers, and then transferring the serum or plasma portion into another container by decantation.

6. The method according to claim 5, wherein the container adapted to be centrifuged is a test tube.

7. A method for separation of a sample of blood into serum or plasma and clot portions which comprises subjecting the blood sample to centrifugation in the presence of a sealant which has a specific gravity of about 1.03 to 1.08 and a viscosity of about 5,000 to 1,000,000 cps at a shearing speed of 1 second$^{-1}$ when measured at 25° C., and consists essentially of (1) a polymer material consisting essentially of units of at least one of unsubstituted alkyl acrylates and unsubstituted alkyl methacrylates, the alkyl moiety having not more than 18 carbon atoms, said polymer material having a specific gravity of 1.000 to 1.030 and a viscosity of not less than about 3,000 cps and less than about 20,000 cps at a shearing speed of 1 second$^{-1}$ when measured at 25° C., and (2) fine powder of silica in an amount of not more than about 30% by weight based on the weight of the polymer material, whereby the blood sample is separated into the serum or plasma portion as the upper layer and the clot portion as the lower layer by intervention of a separator formed by the sealant between the said two layers, and collecting the serum or plasma portion by decantation.

8. The method according to claim 7, wherein the blood sample contains an anticoagulant.

9. A method for separation of a sample of blood into serum or plasma and clot portions which comprises introducing the blood sample into a container adapted to be centrifuged and containing a sealant which has a specific gravity of about 1.03 to 1.08 and a viscosity of about 5,000 to 1,000,000 cps at a shearing speed of 1 second$^{-1}$ when measured at 25° C., and consists essentially of (1) a polymer material consisting essentially of units of at least one of unsubstituted alkyl acrylates and unsubstituted alkyl methacrylates, the alkyl moiety having not more than 18 carbon atoms, said polymer material having a specific gravity of 1.000 to 1.030 and a viscosity of not less than about 3,000 cps and less than about 20,000 cps at a shearing speed of 1 second$^{-1}$ when measured at 25° C., and (2) fine powder of silica in an amount of not more than about 30% by weight based on the weight of the polymer material, subjecting the container to centrifugation whereby the blood sample is separated into the serum or plasma portion as the upper layer and the clot portion as the lower layer by intervention of a separator formed by the sealant between the said two layers, and then transferring the serum or plasma portion into another container by decantation.

10. The method according to claim 9, wherein the container adapted to be centrifuged is a test tube.

11. A method for separation of a sample of blood into serum or plasma and clot portions which comprises introducing a sealant into a container adapted to be centrifuged and containing the blood sample, said sealant being a sealant which has a specific gravity of about 1.03 to 1.08 and a viscosity of about 5,000 to 1,000,000 cps at a shearing speed of 1 second$^{-1}$ when measured at 25° C., and consists essentially of (1) a polymer material consisting essentially of units of at least one of unsubstituted alkyl acrylates and unsubstituted alkyl methacrylates, the alkyl moiety having not more than 18 carbon atoms, said polymer material having a specific gravity of 1.000 to 1.030 and a viscosity of not less than about 3,000 cps and less than about 20,000 cps at a shearing speed of 1 second$^{-1}$ when measured at 25° C., and (2) fine powder of silica in an amount of not more than about 30% by weight based on the weight of the polymer material, subjecting the container to centrifugation whereby the blood sample is separated into the serum or plasma portion as the upper layer and the clot portion as the lower layer by intervention of a separator formed by the sealant between the said two layers, and then transferring the serum or plasma portion into another container by decantation.

12. The method according to claim 11, wherein the container adapted to be centrifuged is a test tube.

* * * * *